United States Patent [19]

Chedid et al.

[11] 4,272,524
[45] * Jun. 9, 1981

[54] N-ACYL-MURAMYL PEPTIDE DERIVATIVES HAVING ANTI-INFECTIOUS INFECTIONS PROPERTIES

[75] Inventors: Louis Chedid; Jean Choay, both of Paris; Edgar Lederer, Sceaux; Pierre Lefrancier, Bures sur Yvette; Monique Parant; Francine Parant, both of Paris, all of France

[73] Assignee: Agence Nationale de Valorisation de la Recherche (ANVAR), Neuilly-sur-Seine-Cedex, France

[*] Notice: The portion of the term of this patent subsequent to Jan. 29, 1997, has been disclaimed.

[21] Appl. No.: 847,673

[22] Filed: Nov. 1, 1977

Related U.S. Application Data

[63] Continuation-in-part of Ser. No. 516,991, Oct. 22, 1974, Pat. No. 4,186,194.

[30] Foreign Application Priority Data

Nov. 2, 1976 [GB] United Kingdom ............... 45597/76

[51] Int. Cl.³ ..................... A61K 37/00; C07C 103/52
[52] U.S. Cl. .............................. 424/177; 260/112.5 R
[58] Field of Search .................. 260/112.5 R; 424/177

[56] References Cited

U.S. PATENT DOCUMENTS

| 4,082,735 | 4/1978 | Jones et al. ........................... 424/88 |
| 4,082,736 | 4/1978 | Jones et al. ........................... 424/88 |

OTHER PUBLICATIONS

F. Ellviz, et al., Biochem. and Biophys. Res. Commun., 59, 1974, pp. 1317-1325.

Ghuysen, et al., Bact. Membranes and Walls, 1973, pp. 39-41.
Chaturvedi, J. Med. Chem., 9, 1966, pp. 971-973.
Kostani, et al., Sympos. Internat'l. or Bact. Immunostimulants, 1973, p. 8.
Lamzelotti, et al., J. Am. Chem. Soc., 86, 1964.
Kotani, et al., Biken J., 13, 105-111, 1975.
Adam, et al., Biochem. and Biophys. Res. Commun., 72, 1976, pp. 339-346.
Chem. Abst., 87, 1977, pp. 199018m, 118075c, 51519e.

Primary Examiner—Delbert R. Phillips
Attorney, Agent, or Firm—Weiser, Stapler & Spivak

[57] ABSTRACT

The invention relates to a new method for increasing the resistance of the organism to pathogenic germs and to compositions to carry out said method.

In this method, one administers an effective dose of N-acetyl-muramyl-L-alanyl-D-isoglutamine or analogs responding to the formula

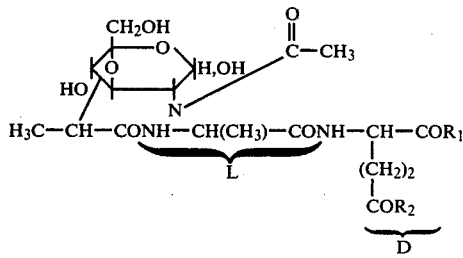

wherein $R_1$ is OH or $NH_2$, $R_2$ is OH, $NH_2$ or a peptidic residue containing from 1 to 6 aminoacids, with the proviso that $R_1$ and $R_2$ are not simultaneously $NH_2$.

25 Claims, No Drawings

N-ACYL-MURAMYL PEPTIDE DERIVATIVES HAVING ANTI-INFECTIOUS INFECTIONS PROPERTIES

BACKGROUND OF THE INVENTION

This application is a Continuation-in-part of the patent application Ser. No. 516,991 now U.S. Pat. No. 4,186,194 filed on Oct. 22, 1974.

The invention relates to a method for increasing the resistance of the organism of a host of pathogenic germs by administering synthetic N-acetyl-muramyl-L-alanyl-D-isoglutamine or analogs.

It is known to be possible to increase the non-specific resistance of a host to infection by injecting the host previously with various immunostimulants of bacterial origin, such as certain strains of Corynebacterium, Mycobacteria and their cord factor, or lipopolyosides (LPS) extracted from Gram-negative bacteria. This protection nevertheless only manifests itself provided that certain intervals of time are respected between the administration of these immunostimulant agents and the time of infection. It has thus been possible to show experimentally that the best survival percentages in mice infected with Klebsiella are observed when the administration of the immunostimulant is effected about 14 days earlier for Bacillus Calmette Guerin (BCG), about 7 days earlier for Corynebacteria, and 6 to 48 hours earlier for LPS. In every case, immunostimulation with the aid of these agents must precede the infection. It is well-known, for example, that, if LPS is injected simultaneously with the bacterial inoculum or afterwards, a "negative reaction" is produced which tends to reduce the resistance of the host which may succumb after the administration of a bacterial strain even if this strain is slightly virulent. On the other hand, if these treatments are administered under good conditions, they stimulate considerably the non-specific immunity even in respect of strains which have been made resistant to antibiotics by mutation or transfer of plasmides. However, it is difficult or even impossible to use these treatments because of the secondary effects observed after the administration of strong doses of Corynebacteria or BCG, and especially because of the toxic effect, in humans, of LPS which represents the toxic antigen of Gram-negative bacteria.

More recently, the studies relating to immunostimulant agents has led to the synthesis of various compounds capable of replacing the adjuvants of bacterial origin, and especially the Mycobacteria in Freund's complete adjuvant (FCA). These compounds have in common a chemical structure of the muramic acid type, to which a short peptidic chain is fixed. They are soluble in water, non-antigenic and non-toxic.

It has also been found that some of these synthetic adjuvants are able to manifest their activity even when administered in the absence of an oily phase, such a phase being necessary for the adjuvant fractions arising from Mycobacteria and in the Freund adjuvant.

On the basis of the results obtained with the aid of the adjuvant agents of bacterial origin, and especially from experiments made with LPS, the properties of these synthetic adjuvants have hitherto only been studied only with respect to preventive immunitary treatments, especially for reinforcing the action of vaccinating compositions containing a weak immunogenic agent.

DETAILED DESCRIPTION OF THE INVENTION

Surprisingly, according to the present invention, it has now been shown that some of the agents having a muramyl peptidic structure have anti-infection properties of the preventive, and even curative type when they are administered on their own, i.e. without a vaccinating composition, especially when they comprise a weak immunogenic agent. In other words, these compounds manifest their properties even when they are administered simultaneously with infection, or even later than the infection which is quite contrary to what is found especially with LPS as referred to above.

According to the invention, there is provided a method for increasing the resistance of the organism of a host to pathogenic germs which comprises administering an effective dose of a compound having the formula

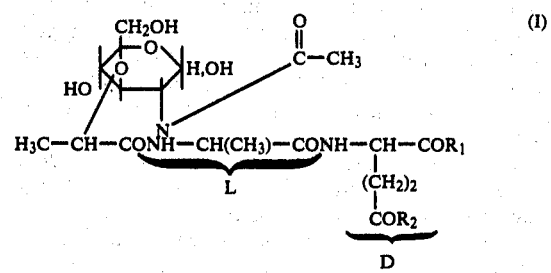

(abbreviated Ac—Mur—L—Ala—D—Glu—$R_1R_2$) wherein $R_1$ is OH or $NH_2$, $R_2$ is OH, $NH_2$ or a peptidic residue containing from 1 to 6 aminoacids, with the proviso that $R_1$ and $R_2$ are not simultaneously $NH_2$.

The abbreviations for these compounds are given according to the recommendation of the IUPAC-IUB Commission on Biochemical Nomenclature (Arch. Biochem. Biophys. 150, 1–8 (1972)).

Preferred compounds for carrying out the method of the invention are those of formula (I) in which $R_2$ is OH or a peptidic residue containing 1 or 2 aminoacids.

Particular examples of compounds exhibiting preventive or curvative anti-infection properties when administered according to the invention are:

| | |
|---|---|
| Ac—Mur—L-Ala—D-Glu—$NH_2$ | (or MDP) |
| Ac—Mur—L-Ala—D-Glu | (or MDPA) |
| Ac—Mur—L-Ala—D-Glu— γ(L-Lys)—$NH_2$ | |
| Ac—Mur—L-Ala—D-Glu— γ(L-Ala)—$NH_2$ | |
| Ac—Mur—L-Ala—D-Glu— γ(L-Lys—L-Ala)—$NH_2$ | |

In addition, as follows from the tests reported in the examples, these compounds have the advantage of being active in the absence of any oily phase, irrespective of whether the administration is made parenterally or orally, whereas the adjuvants such as LPS are only active parenterally.

Accordingly the invention also relates to methods for increasing the resistance of the organism of a host which comprise administering parenterally, orally, rectally or on mucous membrane, a pharmaceutical composition containing at least one compound (I) in a pharmaceutically acceptable vehicle.

Depending on the route of adminstering, the vehicle may be liquid or solid. For oral adminstration recourse is had preferably to solutions, notably aqueous solutions, or to tablets, pills, . . . containing the active compound possibly together with usual adjuvants and/or excipients. for parenteral administration (subcutaneous, intravenous, intramuscular), solutions, and especially isotonic (saline or glucosed) solutions, are preferred. For rectal administration, the composition may be under suppository form, the active compound being associated with usual excipient. Pomades, ointments, salves, balsams, lotions, containing the active compound, may be used on mucous membranes.

The invention also relates to the pharmaceutical composition for the carrying out of the method of the invention. In particular, it relates to aqueous anti-infection injectable compositions containing an effective dose of a compound of formula (I) and most particularly to isotonic saline or glucosed solutions.

The invention also relates to solid or liquid anti-infection compositions for oral administration, containing an effective dose of a compound of formula (I) together with usual adjuvants and excipients. It further relates to compositions for local administration, notably on mucous membranes, of the anti-infection compounds of formula (I).

The products used according to the invention are also devoid of any mitogenic activity (an absence of any blastic transformation of the lymphocytes). They are not antigenic; in fact, they do not release any retarded sensitivity reaction in guinea pigs which have been previously sensitized with the aid of Freund's complete adjuvant. They do not have any hyperthermizing action in rabbits with doses which are very much greater than those for which their anti-infection action manifests itself. They are negative to the Limulus test and their injection does not cause the deaths of the surrenalectomized mice, whereas these mice are made extremely sensitive to the lethal effect of endotoxins by this operation. These results show that these compounds are completely devoid of any endotoxic feature.

The increase in the anti-infection resistance by using these products is obtained, for doses smaller than those needed to obtain the same effect, by means, for example, of sulphadiazine, or in fact a very powerful antibiotic such as streptomycin (the necessary weight ratio of MDP to the latter is approximately 1:3).

The anti-infection curvative activity of these compounds is all the more remarkable and unexpected since the experiments show that they are devoid of any bactericidal or bacteriostatic activity in vitro.

The following tests illustrate the anti-infection properties of the compounds and have been carried out on mice infected with *Klebsiella pneumoniae*.

The mice used for these tests are hybrids (C57B1/6xAKR)F1 bred at the INSTITUT PASTEUR from strains produced from the breeding of the C.N.R.S. in ORLEANS. the endotoxin or LPS has been extracted by the phenol/water method from the Danysz variety of *Salmonella enteritidis*.

The infection by Klebsiella pneumoniae, a strain of the capsular type 2, biotype d, is made from a culture of 16 hours in a medium for pneumococci (No. 53515 INSTITUT PASTEUR). The preparations injected before, or at the time of, the infection are always diluted in some physiological apyrogenic solute, the controls receiving only the solute. The mortalities are recorded for 15 days following the infection.

The anti-infection compounds in question may be prepared for example in the manner described in prior publications, and especially in French patent applications No. 74 22909, 75 29624 and 76 06820 corresponding to the following pending U.S. Pat. applications, respectively, Ser. Nos.: 516,991 (Compositions of Water Soluble Muropeptides and Methods of Administration), 625,195 (Oil Free Adjuvant Compositions Containing N-Acetyl-Muramyl-L-Alanyl-D-Glutamic Acid and Method of Use); and 775,215 (Immunizing and Anti-Infectious Adjuvant Agents Constituted by N-acetyl-muramyl-L-alanyl-D-Glutamic Acid Derivatives.

In a first series of tests, the mice have been infected under conditions corresponding to a very strong inoculation. The preventive anti-infection effect of MDP is studied as a function of the method of administration and the administered dose.

The *Klebsiella pneumoniae* are introduced intravenously at doses of $10^5$ or $10^3$. The MDP is administered 24 hours before the infection.

The results of these tests are given in Table 1. They show very significantly a percentage and a period of survival which are improved in the mice which were treated compared with the controls. This improvement is perceptible even for $10^5$ doses of bacteria and for an oral administration of MDP.

TABLE 1

| Klebsiella pneumoniae i.v. | Treatment (D-1) (doses per animal) µg | | Number of animals treated | Number of survivors | | |
|---|---|---|---|---|---|---|
| | | | | D + 1 | D + 3 | D + 5 |
| | Controls | | 32 | 2 | 1 | 0 |
| $10^5$ | MDP i.v. | 100 | 32 | 9 | 2 | 0 |
| | | 1,000 | 13 | 7 | 6 | 3 |
| | MDP per os | 2,000 | 8 | 7 | 2 | 1 |
| | Controls | | 8 | 6 | 2 | 1 |
| | MDP i.v. | 10 | 8 | 8 | 8 | 7 |
| $10^3$ | | 100 | 8 | 8 | 8 | 7 |
| | | 1,000 | 8 | 8 | 8 | 7 |
| | MDP s/c | 10 | 8 | 8 | 7 | 5 |
| | | 100 | 8 | 8 | 7 | 6 |
| | | 1,000 | 8 | 8 | 8 | 8 |

One important advantage of the anti-infection use according to the invention of the above-mentioned compounds is the possibility of fighting pathogenic germs which have become resistant to antibiotics as a result of treatments by conventional antibiotic means.

In a second series of tests, the compounds were tried on mice which had been infected by an intramuscular injection of $10^4$ *Klebsiella pneumoniae*. The mortality of the mice is noted. It varies between 1 and 8 days subsequent to the inoculation. After 8 days, the survival of the controls as well as the treated animals is definitive.

The products tested are administered 1 day before the infection intravenously, subcutaneously or orally. In a series of tests, the products are administered intravenously 1 hour after the inoculation.

By way of comparison, batches of mice were treated with LPS which, as is well-known, is an extremely active immunostimulant when it is administered 24 hours before the infection.

The results given in Table 2 show that the products which were tried and the LPS very effectively protect the mice treated intravenously (or subcutaneously in the case of MDP and MDPA). However, the LPS is inactive orally, even for very high doses (100 μg of LPS represent 10,000 times the anti-infection dose parenterally), whereas the compounds in question exhibit good protective activity.

The MDP administered after the infection also exhibits its anti-infection properties, whereas under the same conditions, it is known that LPS tends to aggravate the mortality.

TABLE 2

Response to an intramuscular infection by 104 *Klebsiella pneumoniae*

| Treatment | Preparations (doses in μg per animal) | | Number of mice | Survival (%) | | |
|---|---|---|---|---|---|---|
| | | | | D + 3 | D + 5 | D + 8 |
| | Controls | | 16 | 44 | 21 | 0 |
| | LPS | (0.01) | 16 | 100 | 100 | 88 |
| | LPS | (0.1) | 16 | 100 | 100 | 100 |
| | Controls | | 128 | 53 | 29 | 16 |
| | MDP | (10) | 64 | 81 | 69 | 45 |
| | MDP | (100) | 128 | 95 | 79 | 72 |
| | Controls | | 48 | 56 | 33 | 21 |
| | MDPA | (100) | 48 | 100 | 96 | 85 |
| i.v. | Controls | | 40 | 53 | 33 | 18 |
| day-1 | Ac—Mur—L-Ala—D-Glu— (L-Lys)—NH₂ | (100) | 40 | 100 | 93 | 73 |
| | Controls | | 32 | 50 | 47 | 19 |
| | Ac—Mur—L-Ala—D-Glu— (L-Ala)—NH₂ | (100) | 32 | 100 | 94 | 63 |
| | Controls | | 24 | 63 | 46 | 17 |
| | Ac—Mur—L-Ala—D-Glu— (L-Lys—L-Ala) | (100) | 24 | 96 | 79 | 71 |
| | Controls | | 24 | 46 | 29 | 12 |
| | Ac—Mur—L-Ala—D-Glu— γ(NH₂) | (100) | 24 | 92 | 79 | 67 |
| | Controls | | 24 | 42 | 33 | 21 |
| | MDPA | (100) | 24 | 96 | 88 | 75 |
| | Controls | | 16 | 56 | 44 | 19 |
| | MDP | (100) | 16 | 100 | 88 | 75 |
| s.c. | Controls | | 16 | 50 | 38 | 13 |
| day-1 | Ac—Mur—L-Ala—D-Glu— (L-Lys)—NH₂ | (100) | 16 | 100 | 81 | 75 |
| | Controls | | 24 | 67 | 50 | 25 |
| | LPS | (100) | 24 | 50 | 33 | 20 |
| | Controls | | 48 | 63 | 38 | 15 |
| | MDP | (2,000) | 48 | 98 | 90 | 67 |
| per os | Controls | | 32 | 63 | 41 | 25 |
| day-1 | MDPA | (2,000) | 32 | 84 | 72 | 47 |
| | Controls | | 16 | 69 | 56 | 31 |
| | Ac—Mur—L-Ala—D-Glu (L-Lys)—NH₂ | (2,000) | 16 | 81 | 81 | 56 |
| | Controls | | 16 | 44 | 38 | 6 |
| | MDPA | (100) | 16 | 94 | 94 | 75 |
| i.v. | Controls | | 64 | 50 | 25 | 6 |
| | MDP | (100) | 46 | 83 | 67 | 48 |
| hour + 1 | Controls | | 32 | 59 | 47 | 16 |
| | Ac—Mur—L-Ala—D-Glu— (L-Lys)—NH₂ | (100) | 32 | 91 | 78 | 66 |

The present invention therefore provides a method and compositions for increasing the resistance to pathogenic germs and especially for the treatment of infectious diseases by means of compounds which are devoid of any toxicity, these method and compositions being particularly useful by the fact that they are effective in combating pathogenic germs which are resistant to antibiotics.

We claim:

1. The method of controlling infection in a host by causing bactericidal or bacteriostatic activity in the host which comprises administering an effective dose of a compound which is effective to control Klebsiella of the following formula:

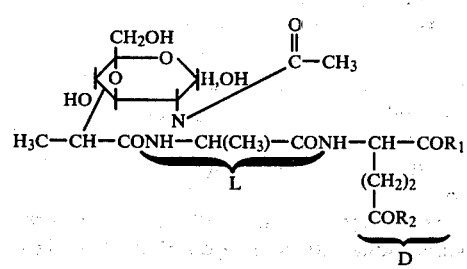

wherein
R₁ is OH or NH₂ and $R_2$ is OH, $NH_2$ or a peptidic residue containing from 1 to 2 aminoacids, wherein the first of said amino acids is L—Ala or L—Lys, with the proviso that $R_1$ and $R_2$ are not simultaneously $NH_2$.

2. The method according to claim 1, wherein $R_2$ is OH or a peptidic residue containing 1 or 2 aminoacids.

3. The method according to claim 1, wherein the compound administered is Ac—Mur—L—Ala—D—Glu.

4. The method according to claim 1, wherein the compound administered is Ac—Mur—L—Ala—D—Glu—$NH_2$.

5. The method according to claim 1, wherein the compound administered is Ac—Mur—L—Ala—D—Glu—γ(L—Lys)—$NH_2$.

6. The method according to claim 1, wherein the compound administered is Ac—Mur—L—Ala—D—Glu—γ(L—Ala)—$NH_2$.

7. The method according to claim 1, wherein the compound administered is Ac—Mur—L—Ala—D—Glu—γ(L—Lys—L—Ala)—$NH_2$.

8. The method according to claim 1, wherein the compound of formula (I) is administered orally in aqueous solution.

9. The method according to claim 1, wherein the compound of formula (I) is administered parenterally in an isotonic saline or glucose solution.

10. The method according to claim 1, wherein said dose is administered to the host infected with said pathogenic microorganisms.

11. The method according to claim 1, wherein said dose is administered to the host after infection with said pathogenic microorganisms.

12. The method according to claim 1 wherein the aqueous solution is oil-free.

13. The method according to claim 1 wherein the Klebsiella are *Klebsiella pneumoniae.*

14. The method of claim 1, wherein said pathogenic microorganisms have become resistant to antibiotics as a result of treatments by conventional antibiotic means.

15. The method of claim 1 wherein the compound is selected from the group consisting of
Ac—Mur—L—Ala—D—Glu—$NH_2$,
Ac—Mur—L—Ala—D—Glu,
Ac—Mur—L—Ala—D—Glu—γ(L—Lys)—$NH_2$,
Ac—Mur—L—Ala—D—Glu—γ(L—Ala)—$NH_2$, and
Ac—Mur—L—Ala—D—Glu—γ(L—Lys—L—Ala)—$NH_2$.

16. The method of claim 15 wherein the administration is oral.

17. The method of claim 16 wherein the administration is made prior to the infection of the host.

18. The method of claim 16 wherein the administration is made when the host is already infected.

19. A composition which has bactericidal or bacteriostatic activity which comprises a pharmaceutically acceptable carrier and, in a bactericidal or bacteriostatic amount a compound selected from the group consisting of:
(1) Ac—Mur—L—Ala—D—Glu—γ(L—Lys)—$NH_2$,
(2) Ac—Mur—L—Ala—D—Glu—γ(L—Ala)—$NH_2$, and
(3) Ac—Mur—L—Ala—D—Glu—γ(L—Lys—L—Ala)—$NH_2$.

20. The composition of claim 19 wherein the carrier is aqueous and oil-free.

21. The composition of claim 19 which is free of an immunogen.

22. The composition of claim 19 wherein the compound is Ac—Mur—L—Ala—D—Glu—γ(L—Lys)—$NH_2$.

23. The composition of claim 19 wherein the compound is Ac—Mur—L—Ala—D—Glu—γ(L—Ala)—$NH_2$.

24. The composition of claim 19 wherein the compound is Ac—Mur—L—Ala—D—Glu—γ(L—Lys—L—Ala)—$NH_2$.

25. The composition of claim 19 which is active against Klebsiella.

* * * * *